US009440911B2

(12) United States Patent
Lunzer et al.

(10) Patent No.: US 9,440,911 B2
(45) Date of Patent: Sep. 13, 2016

(54) MULTIFUNCTIONAL PRIMARY AMINE, PROCESS FOR ITS PREPARATION, AND USE THEREOF

(75) Inventors: Florian Lunzer, Graz (AT); Rudolf Schipfer, Graz (AT); Günther Monschein, Kalsdorf (AT); Ursula Meisner, Graz (AT); Albine Kernbichler, Graz (AT)

(73) Assignee: ALLNEX AUSTRIA GMBH, Werndorf (AT)

( * ) Notice: Subject to any disclaimer, the term of this patent is extended or adjusted under 35 U.S.C. 154(b) by 0 days.

(21) Appl. No.: 14/114,813

(22) PCT Filed: May 3, 2012

(86) PCT No.: PCT/EP2012/058172
§ 371 (c)(1),
(2), (4) Date: Oct. 30, 2013

(87) PCT Pub. No.: WO2012/150312
PCT Pub. Date: Nov. 8, 2012

(65) Prior Publication Data
US 2014/0350141 A1    Nov. 27, 2014

(30) Foreign Application Priority Data
May 5, 2012 (EP) .................................... 11165022

(51) Int. Cl.
| | | |
|---|---|---|
| *B05D 1/00* | (2006.01) | |
| *C08G 59/50* | (2006.01) | |
| *C08K 3/20* | (2006.01) | |
| *C08K 3/22* | (2006.01) | |
| *C08K 3/34* | (2006.01) | |
| *C08L 63/00* | (2006.01) | |
| *C08L 63/02* | (2006.01) | |
| *C07C 225/20* | (2006.01) | |
| *C08G 59/18* | (2006.01) | |
| *C09D 163/00* | (2006.01) | |
| *C07C 221/00* | (2006.01) | |
| *C08K 3/04* | (2006.01) | |
| *C08K 5/06* | (2006.01) | |
| *C08K 5/55* | (2006.01) | |

(52) U.S. Cl.
CPC ........... *C07C 225/20* (2013.01); *C07C 221/00* (2013.01); *C08G 59/184* (2013.01); *C08G 59/502* (2013.01); *C08K 3/04* (2013.01); *C08K 3/20* (2013.01); *C08K 3/22* (2013.01); *C08K 3/34* (2013.01); *C08K 3/346* (2013.01); *C08K 5/06* (2013.01); *C08K 5/55* (2013.01); *C08L 63/00* (2013.01); *C09D 163/00* (2013.01); *B05D 2401/20* (2013.01); *B05D 2504/00* (2013.01); *C08K 2003/2241* (2013.01)

(58) Field of Classification Search
None
See application file for complete search history.

(56) References Cited

U.S. PATENT DOCUMENTS

| | | |
|---|---|---|
| 4,197,389 A | 4/1980 | Becker et al. |
| 4,198,331 A | 4/1980 | Buchwalter et al. |
| 4,454,265 A | 6/1984 | Tortorello et al. |
| 5,097,070 A | 3/1992 | Lin et al. |
| 5,288,802 A | 2/1994 | Walters et al. |
| 6,258,919 B1 | 7/2001 | Vogel et al. |
| 8,143,331 B2 | 3/2012 | Raymond et al. |
| 2003/0001135 A1 | 1/2003 | Gerlitz et al. |
| 2008/0188591 A1 | 8/2008 | Raymond et al. |
| 2011/0195195 A1 | 8/2011 | Geisberger et al. |

FOREIGN PATENT DOCUMENTS

| | | | |
|---|---|---|---|
| CA | 2203313 A | * | 10/1997 |
| CN | 101735706 A | * | 6/2010 |
| CN | 102031051 A | * | 4/2011 |
| EP | 0 000 605 | | 2/1979 |
| EP | 0 272 595 | | 6/1988 |
| EP | 0 301 716 | | 2/1989 |
| EP | 0 346 742 | | 12/1989 |
| EP | 0 426 383 | | 5/1991 |
| EP | 2 028 244 | | 2/2009 |
| EP | 2 058 172 | | 5/2009 |
| EP | 2 520 599 | | 11/2012 |
| GB | 2 028 830 | | 3/1980 |
| JP | 59-174656 | | 10/1984 |
| JP | 10-95954 | | 4/1998 |
| JP | 11-228807 A | * | 8/1999 |
| JP | 2008-248227 | | 10/2008 |
| WO | 97/33931 | | 9/1997 |
| WO | 2010/035641 | | 4/2010 |
| WO | 2011/118792 | | 9/2011 |

OTHER PUBLICATIONS

Chemical Book, "Bisphenol-A-Type Epoxy Resins (E44, E51," 2010, one page.*
International Search Report issued Aug. 7, 2012 in International (PCT) Application No. PCT/EP2012/058172.
Burton et al., "Epox formualtions using Jeffamine Polyetheramines", URL: http://www.huntsman.com/performance_ products/Media/Epoxy_Formulations_Using_JEFFAMINE_ Polyetheramines.pdf, retrieved Sep. 7, 2011.
International Search Report issued Jun. 17, 2014 in International (PCT) Application No. PCT/EP2013/073096.

* cited by examiner

*Primary Examiner* — Robert Sellers
(74) *Attorney, Agent, or Firm* — Wenderoth, Lind & Ponack, L.L.P.

(57) ABSTRACT

The invention relates to a hydrophilically modified multifunctional amine AC which has more than one primary amino group per molecule, and at least one group per molecule derived from the reaction of an epoxide group with a reactive group selected from the group consisting of secondary amino groups >NH, hydroxyl groups —OH, mercaptan groups —SH, amide groups —CO—NHR, where R can be hydrogen or an alkyl group having from one to twelve carbon atoms, hydroxyester groups, and acid particularly carboxyl groups —COOH, sulphonic acid groups —$SO_3H$, and phosphonic acid groups —$PO_3H_2$, and preferably, also moieties which are compatible with an epoxy resin, as well as a process for its preparation, and a method of use thereof.

15 Claims, No Drawings

MULTIFUNCTIONAL PRIMARY AMINE, PROCESS FOR ITS PREPARATION, AND USE THEREOF

FIELD OF THE INVENTION

This invention relates to a multifunctional primary amine, to a process for its preparation, and to a method of use thereof.

BACKGROUND OF THE INVENTION

Aqueous coating binders based on epoxy resins have been used in the coatings industry for many years. Two-pack epoxy coating compositions, both solvent-borne and water-borne, are used particularly for heavy duty corrosion protection of metal substrates, with preference on base metals that do not have other corrosion protection such as zinc coating. Such systems dry quickly providing a tough protective coating with excellent hardness. Coating compositions based on epoxy resins are used mainly for factory-cast iron, cast steel, and cast aluminium parts. The use of water-borne epoxy resin systems reduces exposure and flammability issues associated with solvent-borne coatings, as well as liberation of solvents upon application. Coating compositions based on epoxy resins are mainly used in automotive and industrial applications, such as pipelines, and fittings, due to their heat resistance, chemical resistance and also, mechanical strength. Other uses of epoxy resin-based coating compositions are, for example, in can coating for acidic goods. Coating compositions based on epoxy resins are also widely used as primers to improve the adhesion of paints especially on metal surfaces in automotive and marine applications where corrosion resistance is important. They can also be used for high performance and decorative flooring applications such as industrial floorings, and architectural floorings such as terrazzo.

Water-based epoxy coating compositions usually comprise a hydrophilically modified epoxy resin, and a compatible curing agent which itself is also hydrophilically modified. This hydrophilic modification of epoxy resins is usually effected by introduction of non-ionic hydrophilic moieties. The reason is that the commonly used ionic hydrophilising groups such as amino groups or acid groups which form ions in aqueous environment are reactive themselves with epoxide groups. Introduction of the commonly used poly(oxyethylene) blocks as hydrophilising moiety is a difficult step as strong acid catalysts, mostly Lewis acids such as boron trifluoride, or complexes thereof with ethers or amines, have to be used, and the process is difficult to control. Such chemistry has been described in EP 0 272 595 B1, and also, in EP 0 346 742 B1, for epoxy resins, and i. a. in EP 0 000 605 B1, for curing agents based on adducts of epoxide-functional compounds and amines.

Amine based curing agents for epoxy resins usually have primary, secondary, or also tertiary, amino groups that react with an epoxide group under formation of a beta-hydroxy amine structure or a betaine structure. The curing activity decreases from primary to secondary to tertiary amines. While it is possible to use multifunctional primary amines which are the most efficient amines due to their higher reaction rate, such as isophorone diamine or meta-xylylene diamine, as curing agents for epoxide-functional compounds, their high vapour pressure and unfavourable smell together with potential health hazards has barred their use in applications where no sufficient ventilation is available. Moreover, lack of compatibility of monomeric amines with epoxy resins has limited their usefulness. Secondary amines which stem from reaction of primary amines with epoxide-functional compounds have good compatibility with epoxy resins, yet suffer from lower curing speed compared to that of primary amines.

It has therefore been the object of this invention to provide a multifunctional primary amine that can be used as curing agent in a curable epoxy resin system comprising an epoxide functional compound and an amine-based curing agent therefor, which has both good compatibility and fast curing speed in combination with the said epoxy resin, and further, dispenses with the need to hydrophilically modify both curing agent and epoxy resin.

This problem has been solved by providing hydrophilically modified multifunctional amines having at least two primary amino groups, which amines can be used as curing agents for epoxy resins. These amines can be combined with epoxy resins which need not have hydrophilic modification of their own, or at least no modification which suffices to disperse these epoxy resins themselves without the use of additional emulsifiers in an aqueous phase, and keep the epoxy resin stably dispersed in aqueous dispersions.

By a "hydrophilically modified" compound in the context of this invention, a chemical compound (including oligomeric or polymeric substances having a number average molar mass of at least 350 g/mol) is meant which comprises in its molecules, moieties of oligo- or poly-oxyethylene segments, optionally in mixture with polyoxypropylene segments, in a sufficient amount to keep the said compound stably dispersed in aqueous dispersion for at least one week at room temperature (23° C.), i. e. without phase separation or formation of precipitate visible with the naked eye.

Two substances X and Y are considered compatible for the purpose of this invention if they do not form separate phases after mixing and then letting rest for not less than one hour, in a mass ratio m(X):m(Y) of from 1:99 to 50:50, where m(i) is the mass of substance i, i standing for X or Y. A moiety Z is considered to be compatible with an other substance if a chemical compound consisting essentially of the moiety Z under consideration is compatible with the said other substance. A chemical compound W is considered to consist essentially of a moiety Z if the moiety Z under consideration provides a mass fraction of at least 50%, preferably of at least 70%, and more preferably, of at least 80%, of the said chemical compound W.

SUMMARY OF THE INVENTION

The invention provides a hydrophilically modified multifunctional amine AC which may be used as curing agent for epoxy resins, which multifunctional amine AC has more than one primary amino group per molecule and at least one group per molecule derived from the reaction of an epoxide group with a reactive group selected from the group consisting of secondary amino groups >NH, hydroxyl groups —OH, mercaptan groups —SH, amide groups —CO—NHR, where R can be hydrogen or an alkyl group having from one to twelve carbon atoms, hydroxyester groups, and acid groups, particularly carboxyl groups —COOH, sulphonic acid groups —SO$_3$H, and phosphonic acid groups —PO$_3$H$_2$, and preferably, also moieties which are compatible with an epoxy resin. These groups derived from the reaction of an epoxide group with a reactive group selected from the group consisting of secondary amino groups >NH, hydroxyl groups —OH, mercaptan groups —SH, amide groups —CO—NHR, where R can be hydrogen or an alkyl group having from one to twelve carbon atoms, and acid groups, particularly carboxyl groups —COOH, sulphonic acid groups —SO$_3$H, and phosphonic acid groups —PO$_3$H$_2$ are the following:

a tertiary hydroxyamine, a hydroxyether, a hydroxymercaptane, a a hydroxyamide, and a hydroxyester, where the hydroxy group is in α- or β-position to the amino, mercaptane, amide or ester group.

The multifunctional amine AC has more than one, preferably at least two, primary amino groups per molecule. The term "multifunctional amine" also comprises mixtures of amines, wherein there is an average of more than one, preferably at least two, primary amino groups per molecule. In a further preferred embodiment, the multifunctional amine AC has at least three primary amino groups, and particularly preferred, at least four primary amino groups.

A further object of the invention is a multi-step process to prepare a hydrophilically modified multifunctional amine AC having more than one primary amino group per molecule, by formation, in the first step, of an amino functional compound AB having blocked primary amino groups through reaction of an amine A having at least one primary amino group per molecule, and a further reactive group, preferably selected from the group consisting of secondary amino groups >NH, hydroxyl groups —OH, mercaptan groups —SH, amide groups —CO—NHR, where R can be hydrogen or an alkyl group having from one to twelve carbon atoms, hydroxyester groups, and acid groups, particularly carboxyl groups —COOH, sulphonic acid groups —SO$_3$H, and phosphonic acid groups —PO$_3$H$_2$, with a blocking agent B for the primary amino groups, preferably an aldehyde or a ketone, to form a compound which does not have residual primary amino groups, preferably, a Schiff base which may be an aldimine or ketimine, and reacting, in the second step, the amino functional compound AB having blocked primary amino groups and further reactive groups as detailed supra, with a multifunctional compound C which has functional groups which react with the further reactive groups of the amine A, which is also hydrophilic, and preferably, is also compatible with an epoxy resin, to form an amino-functional compound ABC which has blocked primary amino groups.

A still further object of the invention is an aqueous coating binder comprising an epoxide functional resin E, and a curing agent therefor which has more than one primary amino group per molecule, and which is compatible with an epoxy resin.

A still further object of the invention is a method of use of the multifunctional primary amine AC as a curing agent for epoxide resins E, comprising dispersing the multifunctional primary amine AC in water, optionally at least partially neutralising the dispersion of the multifunctional primary amine AC by addition of acid, adding an epoxide resin E to the aqueous dispersion of the multifunctional primary amine AC, homogenising the mixture ACE thus formed, and applying the mixture ACE to the surface of a substrate.

DETAILED DESCRIPTION OF THE PREFERRED EMBODIMENTS

In a preferred embodiment, the amino-functional compound ABC which has blocked primary amino groups can be deblocked to form a hydrophilically modified multifunctional amine AC by heating, of by addition of a deblocking compound D which liberates the blocked primary amino group. A particularly preferred choice for this deblocking compound D is water which hydrolyses a ketimine or aldimine under splitting off of the ketone or aldehyde, and re-formation of the primary amino groups in the hydrophilically modified multifunctional amine AC.

The hydrophilically modified multifunctional amine AC comprises a structural part derived from an amine, and a structural part that provides solubility or dispersibility in water, and preferably, a further structural part that provides compatibility with an epoxy resin.

In a preferred embodiment, hydrophilic modification is provided by incorporating into the amine AC, moieties derived from polyethylene glycols, from polypropylene glycols, or from oxyethylene-oxypropylene copolymers. These can be linked to the amine part by linking groups which may be derived from diepoxides such as the diglycidyl ether of aliphatic dihydric or polyhydric alcohols, the diglycidyl ether of bisphenol A, the diglycidyl ether of bisphenol F, or the diglycidyl ether of bisphenol S, the diglycidyl esters of dicarboxylic or polycarboxylic acids, from di- or polyfunctional aziridines, from acid anhydrides such as maleic or tetrahydrophthalic or phthalic anhydrides, from acid dichlorides such as terephthalic or isophthalic dichloride, or from diisocyanates such as toluylene diisocyanate or bis(4-isocyanatophenyl)-methane also known as MDI.

In a preferred embodiment of the present invention, the multifunctional amine AC comprises a moiety that is compatible with an epoxy resin by virtue of structural similarity with the said epoxy resin. Such moieties have the same or a similar structure as the backbone of an epoxy resin, and preferably comprise groups by removing hydrogen atoms from hydroxyl groups of the following compounds: bisphenol A, bisphenol F, novolaks derived from phenol or cresol or mixtures of these.

A preferred way of linking the amine part to the hydrophilic part of the amine AC is therefore to use an epoxy functional linking group such as the diglycidyl ether of bisphenol A, or an oligomeric epoxy resin having from two to ten repeating units of formula II infra. This way of linking combines the chemical attachment of amine part and hydrophilic part, and provides the desired compatibility with an epoxy resin at the same time.

An epoxide functional resin, in the context of the present invention, is defined as a resinous substance, having a molar mass of at least 350 g/mol, and at least one epoxide group,

(Formula I)

per molecule.

Preferred epoxy resins E for the purpose of the present invention are epoxy resins based on multivalent phenolic compounds which are etherified with glycidyl alcohol, also referred to as glycidol, which is 2,3-epoxy-1-propanol. It is also possible to use esters of dibasic acids or multibasic acids with glycidol. Useful multivalent phenolic compounds are preferably dihydric phenols such as resorcinol, hydroquinone, 2,2-bis-(4-hydroxyphenyl)propane, also referred to as bisphenol A, bis-(4-hydroxyphenyl)methane, also referred to as bisphenol F, 4,4'-dihydroxybenzophenone, 4,4'-dihydroxydiphenyl sulphone, and also, polyhydric phenolic compounds based on novolaks. Particularly preferred are epoxy resins based on bisphenol A, or on bisphenol F, and also, on mixtures of these. Such epoxy resins are made in the usual way by reacting epichlorohydrin with a multivalent phenolic compound having at least two phenolic hydroxyl groups per molecule, under formation of a structure —[—O—CH$_2$—CH(OH)—CH$_2$—O—Ar—]$_n$—,     (Formula II)

where Ar stands for a divalent aromatic or mixed aromatic-aliphatic radical, which by way of example is —C$_6$H$_4$—C(CH$_3$)$_2$—C$_6$H$_4$—     (Formula III)

in the case of bisphenol A, or by the so-called advancement reaction where, e.g., the di-ether of bisphenol A and glycidol are reacted with further bisphenol A (or other multivalent phenolic compounds). Low molar mass epoxy resins as detailed here are a preferred component C for the present invention.

Structural similarity exists to a high degree if the amine AC comprises a structural element which is equal to that of Formula II, or one is a homologue of the other, such as in the case of a structural element derived from bisphenol A, and a structural element derived from bisphenol F. Another example of structural similarity is an amine AC having a structure [H$_2$N—(CH$_2$)$_4$]$_2$N—CO-Ph-SO$_2$-Ph-CO—(O—CH$_2$—CH$_2$—)$_m$—O—CO-Ph-SO$_2$—CO—N[(CH$_2$)$_4$—NH$_2$]$_2$ which is a tetrafunctional primary amine derived from bis-(4-aminobutyl)amine, polyethylene glycol having a degree of polymerisation m, and sulphonyldibenzoic acid as coupling agent, and an epoxy resin that has moieties derived from bisphenol S also referred to as sulphonyldiphenol, or 4,4'-dihydroxydiphenyl sulphone.

The multifunctional amine AC is hydrophilic which means that it is either water-soluble or water-dispersible. By "water-soluble", a chemical substance is meant that forms a homogeneous single-phase solution in water in a mass fraction range of solute of from 1% to 99%. By "water-dispersible", a chemical substance is meant that forms a stable dispersion in water in a mass fraction range of dispersed substance of from 1% up to the mass fraction at the inversion, and a stable dispersion of water in the said chemical substance up to a mass fraction of at least 60%. The inversion occurs, as is well known to a person skilled in the art, at a volume fraction of about 50%. Below the inversion, the dispersion consists of water as the continuous phase, and the chemical substance as the dispersed phase, and above the inversion, water is the dispersed phase, and the chemical substance is the continuous phase.

In the preparation of the dispersion of the curing agent AC, it is also possible, in a further embodiment, to add monofunctional or multifunctional epoxide-functional compounds having a functionality of one (monofunctional) or of three and higher, to consume a part of the amino groups. Useful mono-epoxy functional compounds are cresyl glycidyl ether, tert.-butylphenyl glycidyl ether, or the glycidyl ether of 2-methyl-2-hexanol, esters of glycidol with monocarboxylic aliphatic acids, particularly 2-ethylhexanoic acid, or highly branched saturated acids such as pivalic acid, 2,2-dimethylbutyric acid, 2,2-dimethylpentanoic acid, 2,2-dimethylhexanoic acid, 2,2-dimethylheptanoic acid, and 2,2-dimethyloctanoic acid, which are commercially available as Versatic® acids, or glycidyl functional silanes such as 3-glycidoxy-propyl-trimethoxysilane. Multifunctional epoxide-functional compounds have a functionality of three or higher are those derived from novolaks which are commercially available as D.E.N.® epoxy novolac resins from The Dow Chemical Company.

Good compatibility of the amines AC with epoxy resins is achieved if there is at least one, preferably between two and five, consecutive units of formula II in the amine AC.

As usual, reaction of a primary amine R—NH$_2$ with an epoxide functional compound always leads to a reaction product where the primary amino group is consumed, under formation of a structure

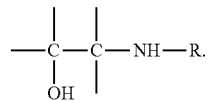

This reaction would consume all primary amino groups, and not lead to the desired functionality. For this reason, the primary amino groups must be protected from reaction with the epoxide groups when reacting the amine A with an epoxy-functional compound. This can be done by a blocking agent B which can be removed, or split off, after the formation of the reaction product between the amine A and the multi-functional compound C.

The amines AC of the present invention having more than one primary amino group per molecule can therefore be made in a multi-step reaction where a multifunctional amine A having more than two primary amino groups, and at least one further reactive group as detailed supra, preferably a secondary amino group, is first reacted with a blocking agent B that reacts selectively with primary amino groups, and does not react with the further reactive groups, particularly not with secondary amino groups. The reaction products AB therefore have only the further reactive groups, preferably secondary amino groups, left as reactive amino groups. In a second step, the secondary amines AB are reacted with the multifunctional, at least difunctional, compounds C that react with the blocked amines AB under formation of adducts ABC which may be of the structure C(AB)$_n$, where n is at least two. In a further embodiment, it is possible to use a substoichiometric amount of AB in the reaction with C. Residual functionality in C may then be reacted with secondary amines A' which do not have blocked primary amino groups, such as dialkylamines or cyclic amines such as piperidine or morpholine, or secondary amines that have additional functionality, such as secondary hydroxyamines, preferably N-alkylalkanolamines such as N-methyl-ethanolamine and 4-hydroxypiperidine, or dihydroxyamines, preferably dialkylolamines such as diethanolamine or dipropanolamine, to form compounds according to C(AB)$_{n-x}$A'$_x$, n being the functionality of C which is at least two, and x being the number of amines A' in one molecule of C(AB)$_{n-x}$A'$_x$. In mixtures of AB and A' being reacted with C, x may, of course, also assume non-integer values.

Preferably, the amines A have primary amino groups that are connected with a methylene group, according to the formula —CH$_2$—NH$_2$. In a preferred embodiment, the amines A may have two primary amino groups, and one secondary amino group as further reactive group. It is preferred to use diprimary monosecondary amines of the formula H$_2$N—(CH$_2$)$_n$—NH—(CH$_2$)$_{n'}$—NH$_2$, with n and n' and n" being integer numbers independently from 2 to 12, preferably from 3 to 8. One or more of the carbon atoms in the alkylene chain may be substituted with alkyl groups having from one to four carbon atoms, or alkoxy groups having from one to four carbon atoms. It is also possible to use amines of the formula H$_2$N—(CH$_2$)$_n$—[NH—(CH$_2$)$_{n'}$]$_{n''}$—NH$_2$.

Preferred are diethylene triamine (1,5-diamino-3-azapentane), triethylene tetramine (1,8-diamino-3,6-diazaoctane), tetraethylene pentamine (1,11-diamino-3,6,9-triazaundecane), dipropylene triamine (1,7-diamino-4-azaheptane), tripropylene tetramine (1,11-diamino-4,8-diazaundecane), dibutylene triamine (1,9-diamino-5-azanonane), tributylene tetramine (1,14-diamino-5,10-diazatetradecane), dihexylene triamine (1,13-diamino-7-azatridecane), and trihexylene tetramine (1,20-diamino-7,14-diazaeicosane), and mixtures of these.

It is also possible to use amines having poly(oxyethylene) or poly(oxypropylene) chains, such as the commercial urea condensates of oligo-oxypropylene diamines $H_2N$—CH($CH_3$)—$CH_2$—[O—CH($CH_3$)—$CH_2$—]$_p$—NH—CO—NH—[$CH_2$—CH($CH_3$)—O—]$_p$—$CH_2$—CH($CH_3$)—$NH_2$, where p may range from 1 to 6. Such amines have the advantage that they already provide sufficient hydrophilicity, the multifunctional compound C is not required to add further hydrophilicity to the amine AC, and needs only to be reactive with the amidic NH groups in the moiety derived from urea.

Particularly preferred amines A are diethylene triamine, N,N-bis(3-aminopropyl)amine, N,N-bis(4-aminobutyl)amine, N,N-bis(5-aminopentyl)amine, N,N-bis(6-aminohexyl)amine, N,N-bis(8-aminooctyl)amine, and N,N-bis(12-aminododecyl)amine, and higher oligomers of these which may be trialkylene tetramines, tetraalkylene pentamines, etc. Mixtures of these can also be used with preference.

It is further preferred that the amine A has two primary amino groups and at least one secondary amino group, and that the multifunctional compound C is difunctional.

In another preferred embodiment, the amine A has one primary amino group and one secondary amino group, and the multifunctional compound C is at least trifunctional.

A further preferred embodiment is when an amine A' is used together with the amine A, wherein the amount of substance of the amine A' is less or equal to the amount of substance of the amine A, and wherein the amine A' has at least one secondary amino group and no primary amino groups. The amine A' is also reacted, together with the amine A, with the multifunctional compound C and leads to a reaction product A'C that can serve as additional compatibiliser.

The blocking agents B are preferably aliphatic aldehydes and ketones having from two to twelve carbon atoms, preferably ketones selected from the group consisting of acetone, methylethyl ketone, diethyl ketone, diisopropyl ketone, and methyl isobutyl ketone. An advantage of blocking with ketones or aldehydes is the cleavage of the Schiff bases formed by the action of water, which is a necessary step when dissolving or dispersing the blocked amine ABC in water. Water is therefore used in this case as the deblocking agent D. The preferred ketones may easily be removed by distillation from the aqueous solution or dispersion of the amine AC. In the reaction to prepare the blocked amine AB, the amount of blocking agent B has to be selected such that a full conversion of the primary amino groups is reached. Full conversion, in the context of this invention, means that at least 95%, preferably at least 98%, and more preferably, at least 99%, of all primary amino groups in the amine A have been reacted with the blocking agent B.

The multifunctional compound C has at least two functional groups selected from the group consisting of carbonylhalogenide —CO—X, where X may be F, Cl, Br, or I, carboxylic acid anhydride —CO—O—CO—, isocyanate —N=C=O, epoxide, and aziridine. Useful multifunctional compounds C are low molar mass epoxy resins, particularly diepoxides, as detailed supra, particularly such diepoxides that are derived from bisphenol A, bisphenol F, and of mixtures of these, such as bisphenol A diglycidyl ether, bisphenol F diglycidyl ether, by reaction with epichlorohydrin. These can be hydrophilically modified by incorporation of oligo- or polyethylene glycol into the epoxy resin, preferably under catalysis with Lewis acids such as boron trifluoride, or chemically bound by reaction with, e.g., difunctional acid halogenides or difunctional acid anhydrides, or with diisocyanates. A preferred way of chemically linking the amine moieties is by using diglycidyl ethers of oligomeric or polymeric oxyethylene glycols or glycols derived from mixtures of ethylene oxide and propylene oxide, or glycidyl ethers of polyfunctional polyethers where polyhydric alcohols such as glycerol or pentaerythritol are reacted with ethylene oxide or propylene oxide, or mixtures of both. A further useful multifunctional compound is an acrylic copolymer where glycidyl(meth)acrylate is one of the comonomers, where the average functionality and also the average degree of polymerisation can be easily controlled to yield the desired functionality.

With particular preference, the multifunctional compound C is selected from the group consisting of halogenides of at least dibasic aromatic or aliphatic or cycloaliphatic acids, of polyglycidyl esters of at least dibasic aromatic or aliphatic or cycloaliphatic acids, of polyglycidyl ethers of at least dihydric phenols, of polyglycidyl ethers of at least dihydric aliphatic or cycloaliphatic alcohols, and of N,O-polyglycidyl hydroxyaromatic amines. If the multifunctional compound C is an epoxide-functional epoxy resin, it is with preference the glycidyl ether of an epoxy resin having at least one repeating units, according to the formula

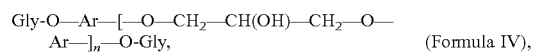

where n is an integer number of at least 0, and Gly-stands for glycidyl,

For the preparation of two-pack epoxy resin systems, the hydrophilically modified amine AC is used as an aqueous solution or dispersion, and the epoxy resin E is then dispersed in the aqueous solution or dispersion of the amine AC. Depending on the degree of hydrophilic modification of the amine AC, it may be needed to add external nonionic emulsifiers, but it is preferred to adjust the amine in a way that it is able to emulsify the epoxy resin added, without the need of adding extra emulsifiers.

It is possible, according to the intended application, to modify the epoxy resin by adding reactive diluents which are mono-epoxy functional compounds such as cresyl glycidyl ether, tert.-butylphenyl glycidyl ether, or the glycidyl ether of 2-methyl-2-hexanol, esters of glycidol with monocarboxylic aliphatic acids, particularly 2-ethylhexanoic acid, or highly branched saturated acids such as pivalic acid, 2,2-dimethylbutyric acid, 2,2-dimethylpentanoic acid, 2,2-dimethylhexanoic acid, 2,2-dimethylheptanoic acid, and 2,2-dimethyloctanoic acid, which are commercially available as Versatic® acids, or glycidyl functional silanes such as 3-glycidoxy-propyl-trimethoxysilane. It is also possible to introduce a limited degree of branching by adding mass fractions of up to 10%, based on the sum of the masses of all epoxide-functional components according to E, of multifunctional epoxides such as those derived from novolaks which are commercially available as D.E.N.® epoxy novolac resins from The Dow Chemical Company.

The two-pack epoxy systems according to this invention may be used for coating of metals, particularly base metals for which they provide excellent corrosion protection, high elasticity, and good hardness. It is believed that this combination of hardness and elasticity is due to the crosslink density which is defined by the average distance between the plurality of primary amino groups in the amine AC.

The aqueous dispersion of the two-pack epoxy system which is made ready for use by dispersing the epoxy resin E in the aqueous solution or dispersion of the amine component AC, and optionally adding additives such as inorganic or organic pigments, functional pigments such as those based on zinc and on phosphate, fillers such as talc, wetting agents, defoamers, antisettling agents, viscosity modifiers, coalescing agents, and UV absorbers.

The two-pack systems made according to the invention are particularly useful for anti-corrosion coating of metals, and also for coating of mineral substrates such as concrete flooring or stone flooring.

The following examples are intended to illustrate the invention without limiting.

The mass fraction of solids $w_s$ was determined by drying a sample B with the mass of 1 g at 125° C. for one hour, and stating the ratio $m_R/m_B$ of the mass $m_R$ of the residue R after drying, and the mass $m_P$ of the sample B taken.

Strength of a solution is stated as the mass fraction $w_B$ of solute B in the solution, calculated as the ratio $m_B/m_S$ of the mass $m_B$ of solute B and the mass $m_S$ of solution S.

The specific content of epoxide groups was determined in the usual way by titration with tetraethylammonium bromide and perchloric acid in glacial acetic acid, as described by R. R. Jay, Anal. Chem. 36, (1964), pages 667 and 668, and stated as the ratio $n(EP)/m_B$ of the amount of substance $n(EP)$ of epoxide groups present in a sample B, and the mass $m_B$ of that sample B; its customary unit is "mol/kg".

The acid number is defined, according to DIN EN ISO 3682 (DIN 53 402), as the ratio $m_{KOH}/m_B$ of that mass $m_{KOH}$ of potassium hydroxide which is needed to neutralise the sample B under examination, and the mass $m_B$ of this sample B, or the mass $m_B$ of the solids in the sample in the case of a solution or dispersion; its customary unit is "mg/g".

Example 1

Preparation of a Ketimine K1

103 g (1 mol) of diethylenetriamine (DETA) and 300 g (3 mol) of methylisobutylketone (MIBK) were charged into a four-necked flask equipped with a mechanical stirrer, a Dean Stark trap, and a gas inlet, and heated to reflux for eight hours under a nitrogen flow. When no more water was collected, the excess MIBK was removed to yield the pure DETA-MIBK-ketimine.

Example 2

Preparation of an Epoxy-Amine Adduct A1

2546 g of bisphenol A diglycidyl ether (BADGE), 450 g of polyethylene glycol with an average molar mass of 1500 g/mol, and 941 g of methoxypropanol were charged into a four-necked flask equipped with a mechanical stirrer and heated to 100° C. under stirring. When this temperature was reached, 3 g of borontrifluoride amine ($BF_3.NH_3$) were charged into the flask and the mixture was heated to 130° C. and maintained at this temperature for two hours until a specific content of epoxide groups of 3.24 mol/kg was reached. The reaction mixture was then cooled to 100° C., and 776 g of bisphenol A and 3 g of triphenylphosphine were charged into the reaction flask. The reaction mixture was then heated again under stirring to 130° C., and was kept at this temperature for two hours until the specific content of epoxide groups in the reaction mixture had reached 1.27 mol/kg. Then, 380 g of methoxypropanol were added, and the reaction mixture was cooled to 80° C. At this temperature, 1335 g of the ketimine K1 of Example 1 were added, and the mixture was stirred for twenty minutes. The mixture was then heated to 90° C., 84 g of diethanolamine were added under stirring, and the mixture was held for twenty minutes at 90° C. 10.2 g of dimethylaminopropylamine were then added, and the reaction mixture was heated to 100° C. and stirred for two hours. 95 g of BADGE were added to scavenge unreacted free amines, and the mixture was stirred at 100° C. for one further hour. After cooling to room temperature (23° C.), the mass fraction of solids was determined to be 80%, and the dynamic viscosity measured at 23° C. and a shear rate of 25 $s^{-1}$ was 5000 mPa·s.

Example 3

Dispersion of Epoxy-Amine Adduct A1 in Water to Prepare Amine Curing Agent Dispersion D1

6624 g of the epoxy amino adduct A1 of Example 2 were heated to 95° C. and neutralised with 429 g of a 50% strength solution of lactic acid in water followed by the addition of 6700 g of water. The solvents methoxypropanol and MIBK were distilled off under reduced pressure of 100 hPa at 60° C. When the distillation of solvent had ceased, 821 g of cresyl glycidyl ether were added to the dispersion, and the mixture was stirred for two hours. The mass fraction of solids of the dispersion was adjusted by addition of 1500 g of water to 35%. The viscosity of the dispersion was 20 mPa·s at 23° C. and a shear rate of 100 $s^{-1}$, the specific content of amine hydrogen atoms was 0.88 mol/kg, its Z-average particle size was 150 nm, and its acid value was 24 mg/g.

Example 4

Preparation of Amine Curing Agent Dispersion D2 to D5

A ketimine K2 was prepared from 1 mol of bis-(6-aminohexyl)-amine and 3 mol of methyl isobutyl ketone as in Example 1.

A further ketimine K3 was prepared from 1 mol of bis-(3-aminopropyl)-amine and 3 mol of methyl isobutyl ketone as in Example 1.

According to the method described in examples 2 and 3, several further curing agent dispersions D2 through D5 were prepared from the epoxy amine adducts A2 through A5 described infra, using the following ingredients:

For the epoxy amine adducts A2, A3, and A4, the procedure of example 2 was used, with the following reactants: 2546 g of BADGE; 450 g of polyethylene glycol having an average molar mass of 1500 g/mol; 628 g of bisphenol A; 1895 g of the ketimine K2; 84 g of diethanolamine; and 97.7 g of N,N-diethylaminopropylamine. For the epoxy amine adduct A5, the procedure of example 2 was used, with the following reactants: 2546 g of BADGE; 450 g of polyethylene glycol having an average molar mass of 1500 g/mol; 628 g of bisphenol A; 1475 g of the ketimine K3; 84 g of diethanolamine; and 97.7 g of N,N-diethylaminopropylamine. Adducts were obtained with a mass fraction of solids of 90%, following addition of 633.41 g of methoxypropanol.

These adducts A2, A3, A4, and A5 were partially neutralised, by adding 462.16 g of an aqueous solution of lactic acid having a strength of 50% (A2, A4, A5) or 513.52 g (A3), and 492.6 g of cresylglycidyl ether (A3), 1250 g of glycidyl neodecanoate (A4), 480 g of glycidyl neodecanoate (A5), or nothing (A2) were added.

TABLE 1

Properties of the Dispersions

| | | Curing Agent Dispersion | | | |
|---|---|---|---|---|---|
| | | D2 | D3 | D4 | D5 |
| mass fraction of solids | $w_s/\%$ | 51.6 | 52.3 | 60.5 | 40 |
| Z-average Particle Diameter | $s/\text{nm}$ | 173 | 260 | 178 | 167 |
| specific content of amine hydrogen | $n_{NH}/\text{mol} \cdot \text{kg}^{-1}$ | 1.946 | 1.55 | 1.4 | 1.41 |

Example 5

Pigment Paste Preparation

The components A of table 2 were mixed in the given order in a vessel equipped with a mechanical stirrer. After homogenising the mixture for ten minutes, it was ground on a bead mill with zirconium oxide beads having a diameter of 1 mm for thirty minutes at 3000/min. Finally, component B was added, and the mixture was homogenised with a mechanical stirrer. The pigment paste obtained had a mass fraction of solids of 75%.

TABLE 2

Ingredients of the Pigment Paste

| Group | Ingredient | Designation | mass in g |
|---|---|---|---|
| A | non-ionic dispersing and wetting agent | ®Additol VXW 6545 (Cytec Austria GmbH) | 17.42 |
| | deionised water | | 40.72 |
| | micronised talc | ®Micro-talc AT1 (Norwegian Talc Minerals A. S.) | 26.94 |
| | kaolin | ®ASP-600 (Engelhard Corporation) | 26.94 |
| | feldspar | ®Minex 10 (Quarzwerke GmbH) | 26.94 |
| | titanium dioxide (rutile) | ®Kronos 2190 (Kronos International Inc.) | 26.94 |
| | carbon black | ®Printex U (Evonik Degussa GmbH) | 0.40 |
| | $(\text{Zn,Al,Mo})\text{PO}_4 \cdot \text{H}_2\text{O}$, organic modified | ®Heucophos ZAM+ (Heubach GmbH) | 28.74 |
| | defoamer | ®Additol VXW 6211 (Cytec Austria GmbH) | 1.58 |
| B | silane based corrosion inhibitor | ®Halox 550 (C. H. Erbslöh SE) | 3.40 |
| | Total | | 200.00 |

Example 6

Paint Preparation

The dispersions D1 through D5 as described in Examples 3 and 4 above were used as curing agents for two-pack epoxy-amine paints. These dispersions were mixed with the pigment paste of Example 5 to give Component 1 of the two-pack system. Just before application of the paints to the substrate, Component 2—a hydrophilically modified epoxy resin—was admixed to Component 1 with a mechanical stirrer. The ratio $n_{NH}/n_{EP}$ of the amount of substance $n_{NH}$ of active N—H groups to the amount of substance $n_{EP}$ of epoxide groups was set to 0.7 mol/1 mol; the mass of pigment paste was chosen such that a ratio of the mass of pigment to the mass of binder of 1.5/1 was achieved in the paints.

Example 6.1

Paint P1

100 g of dispersion D1 were mixed with 70 g of the pigment paste of example 5 and 35 g of deionised water. After stirring the mixture for thirty minutes with a mechanical stirrer, 25 g of an emulsified epoxy resin E1 prepared as a mixture of 618 g of bisphenol A diglycidyl ether "BADGE" and 262 g of bisphenol F diglycidyl ether with 119 g of an emulsifier made by reacting 385 g of polyethylene glycol of average molar mass of 1 kg/mol with 612 g of BADGE and 2 g of boron trifluoride-benzylamine complex; see EP 0 000 605 B1) were added to the stirred mixture. 2 g of n-butoxypropanol were added to improve the film formation. The resulting paint had a mass fraction of solids of 48.5%, and a viscosity of 300 mPa·s, measured at 23° C. and a shear rate of 25 s$^{-1}$.

Example 6.2

Paints P2 and P3

According to the procedure described supra, two-pack paints were prepared from curing agent dispersions D2 and D3, together with the emulsified epoxy resin E1 as described supra.

Example 7

Paint Testing

Paint films were applied from the pigmented paints P1, P2 and P3 of examples 6.1 and 6.2 in a wet layer thickness of 200 μm. The films were cured at room temperature (23° C.) for six hours in each case. The surface after drying was smooth in all cases indicating good compatibility of epoxy resin and curing agent.

The following tests were made on coated substrates: drying time, pendulum hardness according to König, DIN EN ISO 1522, gloss, and chemical resistance measured as MEK double rubs according to ASTM D4752

The following table 3 lists the results measured on pigmented paint films (200 μm)

TABLE 3

Paint Test Results

| Property | | Paint P1 | Paint P2 | Paint P3 |
|---|---|---|---|---|
| Drying | Dust-free | 85 min | 45 min | 50 min |
| Time | Tack-free | 5 h | 4 h | 6 h |
| König | 24 h | 13 s | 73 s | 25 s |
| Hardness | 48 h | 18 s | 98 s | 47 s |
| | 7 d | 48 s | 134 s | 104 s |
| | 14 d | 65 s | 141 s | 107 s |
| | 21 d | 84 s | 158 s | 123 s |
| | 28 d | 97 s | 159 s | 144 s |
| Gloss (60°) | | 79% | 95% | 98% |
| MEK Double Rubs* | | 60 | >200 | >200 |

*MEK double rubs were measured after 28 d of drying

Example 8

Comparative Testing

In order to assess the potential of the novel products in anticorrosion paints, they were compared to epoxy curing agents of the state of the art, CA2 and CA1, each in combination with a waterborne epoxy dispersion of a solid epoxy resin E2 having a mass fraction of solids in the dispersion of 53%, and a specific content of epoxy groups of 1.92 mol/kg ("epoxy equivalent weight" of 520 g/mol), the latter based on the mass of solid resin.

Curing agent CA1, made according to example 3B of EP 0 000 605 B1, is a curing agent for fast drying compositions giving short drying times but no optimised anticorrosion performance.

Curing agent CA2 was made according to example "Aminhärter 1" of EP 1 266 920 B1; this curing agent provides very good anticorrosion performance with epoxy resin dispersions, but has the disadvantage of long drying times.

For testing of the drying times, potlife, and hardness, clearcoat mixtures were made from the curing agent dispersions CA1, CA2, D1, and D2, each combined with epoxy resin dispersion E2, in a ratio n(EP)/n(NH) of the amount of substance n(EP) of epoxy groups in the dispersion E2 to the amount of substance n(NH) of amine hydrogen atoms present in the curing agent dispersions of 0.6 mol/1 mol.

Paints P4 and P5 were prepared by mixing curing agent dispersions D1 and D2, respectively, with the pigment paste of Example 5 which latter mixture was mixed immediately before application onto the substrate with the epoxy resin dispersion E2. Comparative pigmented paints C1 and C2 using the pigment past of Example 5 were combinations of the same epoxy resin dispersion E2 with comparative curing agents CA1 and CA2 as described supra. The ratio $n_{NH}/n_{EP}$ of the amount of substance $n_{NH}$ of amine hydrogen atoms to the amount of substance $n_{EP}$ of epoxide groups was set to 0.6 mol:1 mol, and the mass of pigment paste was chosen such that a ratio of the mass of pigment to the mass of binder of 1.5/1 was achieved in the paints.

Table 4 shows the test results achieved in this comparison. Drying time, pot life and hardness were measured on clear coat paints. To determine the pot life, clearcoat paints were applied to Leneta Paper cards in thirty minute intervals after mixing the two-pack paint, up to a total of three hundred and ninety minutes and the longest time span where no haze had developed was stated as pot life.

TABLE 4

Paint Test Results

| | Two-Pack Clearcoats | | | |
|---|---|---|---|---|
| | CA2 + E2 | CA1 + E2 | D1 + E2 | D2 + E2 |
| dustfree drying time | 2.5 h | 45 min | 30 min | 20 min |
| tackfree drying time | >6 h | 4 h | 4 h | 2 h |
| potlife | 3 h | 1.5 h | 3 h | 2 h |
| pendulum hardness * | 33 s | 128 s | 46 s | 84 s |
| pendulum hardness ** | 75 s | 183 s | 89 s | 122 s |
| Pigmented Paints | C2 | C1 | P4 | P5 |
| saltspray test+ | B 1s2, D 3 . . . 4 | B 2s2, D total | B none, D 10 | B none, D 1 |
| humidity test++ | B 1s2 | B 3s3 | B none | B none |

* after 24 h
** after one week
+according to DIN EN ISO 9227, after two weeks; B = blistering, D = delamination (in mm)
++according to EN ISO 4628-2: 2003, after two weeks; B = blistering
Salt spray test and humidity test were performed on pigmented paints (paint C2; paint C1).

It can be seen that the clearcoats D1+E2 and D2+E2, and the pigmented paints P4 and P5 prepared from the curing agent dispersions D1 and D2 according to the present invention show fast drying, yet an extended pot life, and show an improvement in both humidity resistance and corrosion resistance versus the known systems, as exemplified with clearcoats and pigmented paints using the comparative curing agents.

It is likewise possible to combine the curing agent dispersions according to the present invention with non-modified liquid epoxy resins, where such combinations show drying times on the same scale as combinations of the said liquid epoxy resins with curing agents according to the state of the art, such as curing agents CA1 and CA2 mentioned supra. In contrast to these curing agents of the state of the art, mixtures with the curing agent dispersions of the present invention provide paints that impart good anticorrosion properties to the substrates coated therewith, and the compatibility with unmodified liquid epoxy resins is improved which latter shows in better surface appearance of coated substrates. This is shown in the following examples.

Example 9

Two-Pack Paints with Liquid Epoxy Resins

As per table 5 infra, mixtures were prepared of the curing agent dispersion D3 according to the invention, and of curing agents CA1 and CA2, with a liquid epoxy resin L1 based on a mixture of bisphenol A and bisphenol F, additionally comprising an emulsifier based on a reaction product of polyethylene glycol and bisphenol A diglycidyl ether, and a liquid epoxy resin L2 comprising a mixture of a mass fraction of 70% of bisphenol A diglycidyl ether and 30% of tert.-butylphenyl glycidyl ether as reactive diluent, respectively, and the pigment paste of example 5, and these mixtures were combined with the epoxy resin, as listed, to provide two-pack coating compositions having a ratio $n_{NH}/n_{EP}$ of the amount of substance $n_{NH}$ of amine hydrogen atoms N—H to the amount of substance $n_{EP}$ of epoxide groups of 0.7 mol/1 mol; the mass of pigment paste of example 5 was chosen such that a ratio of the mass of pigment to the mass of binder of 1.5/1 was achieved in the paints.

Paint P31 is the combination of curing agent dispersion D3 with epoxy resin L1, and paint P32 is the combination of D3 with epoxy resin L2. Similarly, C11 is the combination of comparative curing agent CA1 with epoxy resin L1, C12 is the combination of comparative curing agent CA1 with epoxy resin L2, C21 is the combination of comparative curing agent CA2 with epoxy resin L1, and C22 is the combination of comparative curing agent CA2 with epoxy resin L2. In each case, the proper amount of the paste resin of Example 5 was added to the curing agent dispersion before admixing the epoxy resin. Drying time, pendulum hardness and pot life have been determined on unpigmented paints.

TABLE 5

Two-Pack Coating Compositions based on Liquid Epoxy Resins

| Two-Pack Paints | D3 + L1 | D3 + L2 | CA1 + L1 | CA1 + L2 | CA2 + L1 | CA2 + L2 |
|---|---|---|---|---|---|---|
| dustfree drying time | 55 min | 290 min | 30 min | 210 min | § | § |
| tackfree drying time | 5 h | 7 h | 130 min | 480 min | | |
| potlife | >6 h | >6 h | 6 h | separates | | |
| pendulum hardness * | 113 s | 80 s | 87 s | *** | | |
| pendulum hardness ** | 180 s | 143 s | 190 s | *** | | |
| Pigmented paints | P31 | P32 | C11 | C12 | | |
| saltspray test[+] | B none; D 15 . . . 20 | B none; D 4 . . . 10 | B 5s5; D total | B 5s4; D total | | |
| humidity test[++] | 2B 3s3 | 2B 2s2 | 1B 5s5 | 1B 4s5 | | |

* pendulum hardness measured after 24 h
** pendulum hardness measured after seven days
*** surface too inhomogeneous for evaluation
[+]according to DIN EN ISO 9227, after two weeks; B = blistering, D = delamination (in mm)
[++]according to EN ISO 4628-2: 2003, after two weeks; B = blistering
§ two pack composition exhibits phase separation between thirty and sixty minutes after mixing It can be seen that the curing agents comprising the polyfunctional amine according to the invention provide good emulsification that allows to use non-hydrophilically modified epoxy resin, and lead to improved corrosion resistance compared to the state of the art.

The invention claimed is:

1. A hydrophilically modified multifunctional amine AC which has more than one primary amino group per molecule, and at least one group per molecule derived from the reaction of an epoxide group with a reactive group selected from the group consisting of secondary amino groups >NH, mercaptan groups —SH, amide groups —CO—NHR, wherein R can be hydrogen or an alkyl group having from one to twelve carbon atoms, hydroxyester groups, and acid groups, wherein the hydrophilically modified multifunctional amine AC comprises, in its molecules, moieties of oligo- or poly-oxyethylene segments in a sufficient amount to keep the hydrophilically modified multifunctional amine AC stably dispersed in an aqueous dispersion for at least one week at room temperature (23° C.),
wherein the hydrophilically modified multifunctional amine AC is obtained by a process wherein, in the first step, an amino functional compound AB having blocked primary amino groups and no residual primary amino groups is formed through reaction of an amine A having at least one primary amino group per molecule, and a further reactive group, selected from the group consisting of secondary amino groups >NH, mercaptan groups —SH, amide groups —CO—NHR, wherein R can be hydrogen or an alkyl group having from one to twelve carbon atoms, hydroxyester groups, and acid groups, with a blocking agent B for the primary amino groups,
in the second step, the amino functional compound AB is reacted with a multifunctional compound C containing at least two epoxide groups which react with the further reactive groups of the amine A to form an amino-functional compound ABC which has blocked primary amino groups, and
removing the blocking agent B from the compound ABC by heating or by addition of a deblocking compound D which liberates the blocked primary amino group to form the amine AC.

2. The hydrophilically modified multifunctional amine AC of claim 1 which has at least two primary amino groups per molecule.

3. The hydrophilically modified multifunctional amine AC of claim 1, wherein the hydrophilic modification is provided by moieties derived from oxyethylene or from oxyethlene-oxypropylene moieties or their mixtures.

4. A method of use of the multifunctional primary amine AC according to claim 1 as a curing agent for epoxide resins E, comprising dispersing the multifunctional primary amine AC in water, optionally at least partially neutralizing the dispersion of the multifunctional primary amine AC by addition of acid, adding an epoxide resin E to the aqueous dispersion of the multifunctional primary amine AC, homogenising the mixture ACE thus formed, and applying the mixture ACE to the surface of a substrate.

5. The method of use of claim 4 where in the epoxide resin E is a mixture of di-epoxide-functional compounds and at least one of mono-epoxide-functional compounds and epoxide functional compounds having a functionality of at least three.

6. The method of use of claim 4, further comprising adding to the aqueous dispersion of the multifunctional primary amine AC or to the mixture ACE before applying the mixture ACE to the surface of the substrate at least one of pigments, fillers, defoamers, wetting agents, antisettling agents, viscosity modifiers, and coalescing agents.

7. The hydrophilically modified multifunctional amine AC of claim 1, wherein the acid groups are selected from carboxyl groups —COOH, sulphonic acid groups —$SO_3H$, and phosphonic acid groups-$PO_3H_2$.

8. The hydrophilically modified multifunctional amine AC of claim 1 having at least one group per molecule derived from the reaction of an epoxide group with a reactive group selected from the group consisting of secondary amino groups.

9. The hydrophilically modified multifunctional amine AC of claim 1, wherein the amine A has two primary amino groups and at least one secondary amino group, and wherein the multifunctional compound C is difunctional.

10. The hydrophilically modified multifunctional amine AC of claim 1, wherein the amine A is selected from the group consisting of diethylene triamine, triethylene tetramine, tetraethylene pentamine, dipropylene triamine, tripropylene tetramine, dibutylene triamine, tributylene tetramine, dihexylene triamine, and trihexylene tetramine, and mixtures of any of these.

11. The hydrophilically modified multifunctional amine AC of claim 1, wherein an amine A' is used together with the amine A, wherein the amount of substance of the amine A' is less or equal to the amount of substance of the amine A, and wherein the amine A' has at least one secondary amino group and no primary amino groups.

12. The hydrophilically modified multifunctional amine AC of claim 1, wherein the multifunctional compound C is selected from the group consisting of polyglycidyl esters of at least dibasic aromatic or aliphatic or cycloaliphatic acids, of polyglycidyl ethers of at least dihydric phenols, of polyglycidyl ethers of at least dihydric aliphatic or cycloaliphatic alcohols, and of N,O-glycidyl hydroxyaromatic amines.

13. The hydrophilically modified multifunctional amine AC of claim 1, wherein the multifunctional compound C is the polyglycidyl ether of an epoxy resin having at least one repeating unit.

14. The hydrophilically modified multifunctional amine AC of claim 1, wherein the amine A has one primary amino group and one secondary amino group, and wherein the multifunctional compound C is at least trifunctional.

15. The hydrophilically modified multifunctional amine AC of claim 1, wherein the blocking agent is selected from the group consisting of an aldehyde or a ketone.

* * * * *